(12) United States Patent
Heo et al.

(10) Patent No.: US 9,784,747 B2
(45) Date of Patent: Oct. 10, 2017

(54) METHOD AND KIT FOR ANALYZING PROTEIN-PROTEIN INTERACTION USING NANOCLUSTER FORMATION

(75) Inventors: Won Do Heo, Daejeon (KR); Sun Chang Kim, Daejeon (KR); Sang Kyu Lee, Seoul (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 14/234,243

(22) PCT Filed: Jul. 23, 2012

(86) PCT No.: PCT/KR2012/005868
§ 371 (c)(1),
(2), (4) Date: Aug. 21, 2014

(87) PCT Pub. No.: WO2013/015589
PCT Pub. Date: Jan. 31, 2013

(65) Prior Publication Data
US 2015/0044712 A1 Feb. 12, 2015

(30) Foreign Application Priority Data
Jul. 22, 2011 (KR) .................. 10-2011-0073067

(51) Int. Cl.
| | | |
|---|---|---|
| *G01N 33/68* | (2006.01) | |
| *C12N 15/10* | (2006.01) | |
| *C12N 15/79* | (2006.01) | |
| *G01N 33/58* | (2006.01) | |

(52) U.S. Cl.
CPC ..... *G01N 33/6845* (2013.01); *C12N 15/1055* (2013.01); *C12N 15/79* (2013.01); *G01N 33/582* (2013.01); *C07K 2319/00* (2013.01); *C07K 2319/60* (2013.01); *C07K 2319/735* (2013.01); *G01N 2333/91205* (2013.01)

(58) Field of Classification Search
None
See application file for complete search history.

(56) References Cited

U.S. PATENT DOCUMENTS

2010/0273673 A1* 10/2010 Kim .................. G01N 33/5008
506/9

FOREIGN PATENT DOCUMENTS

EP          1 645 881 A1 *  4/2006  ............. G01N 33/58

OTHER PUBLICATIONS

Lee et al., "Visualizing dynamic interaction between calmodulin and calmodulin-related kinases via a monitoring method in live mammalian cells" 107(8) Proceedings of the National Academy of Sciences USA 3412-3417 (2010) (Including Supplemental Material).*
Finnen et al., "Interactions between Papillomavirus L1 and L2 Capsid Proteins" 77(8) Journal of Virology 4818-4826 (2003).*

* cited by examiner

*Primary Examiner* — Nancy J Leith
(74) *Attorney, Agent, or Firm* — Ladas & Parry LLP

(57) ABSTRACT

For efficient analysis of a protein-protein interaction, the present disclosure provides a kit for analyzing a protein-protein interaction, the kit including: a $1^{st}$ expression vector including a $1^{st}$ polynucleotide and a multi-cloning site, wherein, the $1^{st}$ polynucleotide is operably linked to a promoter and encodes a $1^{st}$ fusion protein having a $1^{st}$ fluorescence protein and a $1^{st}$ self-assembly protein, and the multi-cloning site is a site where a polynucleotide encoding a bait protein may be operably linked to the polynucleotide encoding the $1^{st}$ fusion protein; and a $2^{nd}$ expression vector including a $2^{nd}$ polynucleotide and a multi-cloning site, wherein, the $2^{nd}$ polynucleotide is operably linked to a promoter and encodes a $2^{nd}$ fusion protein having a $2^{nd}$ fluorescence protein and a $2^{nd}$ self-assembly protein, and the multi-cloning site is a site where a polynucleotide encoding a prey protein may be operably linked to the polynucleotide encoding the $2^{nd}$ fusion protein.

24 Claims, 8 Drawing Sheets a b a

DsRed-HRas        RBD_{Raf1}-ECFP-FT        Merged b

DsRed-HRas        CRIB_{WASP}-ECFP-FT        Merged

→ Negative control

METHOD AND KIT FOR ANALYZING PROTEIN-PROTEIN INTERACTION USING NANOCLUSTER FORMATION

TECHNICAL FIELD

The present disclosure relates to a method and a kit for analyzing a protein-protein interaction, and more particularly, to a method and a kit for analyzing a protein-protein interaction using a nanocluster formation.

BACKGROUND ART

Generally, various physiological functions are regulated by dynamic interactions between various physiological active materials. Abnormal occasions when these interactions do not properly occur or molecules of which interactions are not desired interact with each other, may result in diseases. Generally, two proteins having complementary structures interact with each other, and a physiological active compound specifically interacts with a protein having tertiary structure at a particular site. Since the physiological active compound regulates a function of a heterologous protein, the physiological active compound may be a candidate material for a therapeutic agent which may diagnose, prevent, or treat and alleviate a disease associated with the protein.

A study has been continued for screening a target or a therapeutic agent of disease by analyzing a protein-protein interaction and an interaction between a protein and a small molecule compound. As an example, techniques such as phagedisplay (Sche at al., Chem. Biol., 6: 707, 1999), yeast two-/three-hybrid assay (Licitra et al., Proc. Natl. Acad. Sci. USA, 93: 12817, 1996), and parallel analysis of a yeast strain having heterologous deletion (Zheng et al., Chem. Biol., 11: 609, 2004) may be included. However, these techniques have problems such as high background, false-positive, and low sensitivity. Also, the test result is not 100% reliable for reaction using non mammalian cells or in vitro reaction.

Korean Patent Publication No. 2009-0018585, which is derived to overcome such problems, relates to a method for investigating presence and absence of interactions between a bait protein and a prey protein through a difference in a luminescence pattern due to a cluster formation of self assembled fluorescence nanoparticles after simultaneously expressing a $1^{st}$ fusion protein and a $2^{nd}$ fusion protein in one cell line, wherein the $1^{st}$ fusion protein is a ferritin protein capable of self-assembly to which a fluorescence protein and the bait protein is linked, and the $2^{nd}$ fusion protein is a ferritin protein to which the same fluorescence protein and the prey protein is linked.

DISCLOSURE OF THE INVENTION

Technical Problem

However, in the technique disclosed in Korean Patent Publication No. 2009-0018585, both a bait protein and a prey protein are present in one nanoparticle. Thus, false-negative, which refers a condition that interactions between nanoparticles are inhibited by interactions between the bait protein and the prey protein in a single nanoparticle, may be exhibited (FIG. 1a). On the contrary, false-positive may be exhibited by homodimerization between the bait proteins or the prey proteins which are present in a different nanoparticle (FIG. 1b).

The present disclosure is to solve various problems including the problem described above and directed to provide a method and a kit for analyzing a protein-protein interaction using a nanocluster formation. However, these solutions are illustrative purpose only, and the scope of the present disclosure is not limited thereto.

Technical Solution

According to an aspect of the present disclosure, provided is a kit for analyzing a protein-protein interaction including: a 1st expression vector including a 1st gene construct having a 1st polynucleotide operably linked to a promoter and encodes a $1^{st}$ fusion protein having a bait protein, a $1^{st}$ fluorescence protein and a $1^{st}$ self-assembly protein; and a $2^{nd}$ expression vector including a $2^{nd}$ gene construct having a $2^{nd}$ polynucleotide operably linked to a promoter, and encodes a $2^{nd}$ fusion protein having a prey protein, a $2^{nd}$ fluorescence protein and a $2^{nd}$ self-assembly protein, the kit being characterized in that: the $1^{st}$ fluorescence protein and the $2^{nd}$ fluorescence protein emit light having different wavelengths from each other; the $1^{st}$ self-assembly protein and the $2^{nd}$ self-assembly protein do not interact with each other; and the $1^{st}$ fluorescence protein or the $2^{nd}$ fluorescence protein is omittable in the case where either the $1^{st}$ fluorescence protein or the $2^{nd}$ fluorescence protein is DsRed.

According to another aspect of the present disclosure, provided is a kit for analyzing a protein-protein interaction including: a $1^{st}$ expression vector including a $1^{st}$ polynucleotide and a multi-cloning site, wherein, the $1^{st}$ polynucleotide is operably linked to a promoter and encodes a $1^{st}$ fusion protein having a $1^{st}$ fluorescence protein and a $1^{st}$ self-assembly protein, and the multi-cloning site is a site where a polynucleotide encoding a bait protein may be operably linked to the polynucleotide encoding the $1^{st}$ fusion protein; and a $2^{nd}$ expression vector including a $2^{nd}$ polynucleotide and a multi-cloning site, wherein, the $2^{nd}$ polynucleotide is operably linked to a promoter and encodes a $2^{nd}$ fusion protein having a $2^{nd}$ fluorescence protein and a $2^{nd}$ self-assembly protein, and the multi-cloning site is a site where a polynucleotide encoding a prey protein may be operably linked to the polynucleotide encoding the $2^{nd}$ fusion protein, the kit being characterized in that the 1st fluorescence protein and the $2^{nd}$ fluorescence protein emit light having different wavelengths from each other; the 1st self-assembly protein and the $2^{nd}$ self-assembly protein do not interact with each other; and the $1^{st}$ fluorescence protein or the $2^{nd}$ fluorescence protein is omittable in the case where either the $1^{st}$ fluorescence protein or the $2^{nd}$ fluorescence protein is DsRed.

According to another aspect of the present disclosure, provided is a method for analyzing a protein-protein interaction, the method including: transfecting a cell with a $1^{st}$ expression vector including a $1^{st}$ gene construct and a $2^{nd}$ expression vector including a $2^{nd}$ gene construct, wherein the 1st gene construct including a $1^{st}$ polynucleotide which is operably linked to a promoter and encodes a $1^{st}$ fusion protein having a bait protein, a $1^{st}$ fluorescence protein and a $1^{st}$ self-assembly protein, and the $2^{nd}$ gene construct including a $2^{nd}$ polynucleotide which is operably linked to a promoter and encodes a $2^{nd}$ fusion protein having a prey protein, a $2^{nd}$ fluorescence protein and a $2^{nd}$ self-assembly protein; and observing fluorescence distribution and intensity in the cell with a fluorescence microscopy after culturing the transfected cell, the method being characterized in that: the $1^{st}$ fluorescence protein and the $2^{nd}$ fluorescence protein emit light having different wavelengths from each other; the $1^{st}$ self-assembly protein and the $2^{nd}$ self-assembly protein do not interact with each other; and the $1^{st}$ fluorescence protein or the $2^{nd}$ fluorescence protein is omittable in the case where either the $1^{st}$ fluorescence protein or the $2^{nd}$ fluorescence protein is DsRed.

According to another aspect of the present disclosure, provided is a method for analyzing a protein-protein interaction, the method including: transfecting a cell with a $1^{st}$ expression vector including a $1^{st}$ gene construct and a $2^{nd}$ expression vector including a $2^{nd}$ gene construct, wherein the $1^{st}$ gene construct including a $1^{st}$ polynucleotide which is operably linked to a promoter and encodes a $1^{st}$ fusion protein having a bait protein, a $1^{st}$ fluorescence protein and a $1^{st}$ self-assembly protein, and the $2^{nd}$ gene construct including a $2^{nd}$ polynucleotide which is operably linked to a promoter and encodes a $2^{nd}$ fusion protein having a prey protein, a $2^{nd}$ fluorescence protein and a $2^{nd}$ self-assembly protein; treating the transfected cell with a candidate material for regulating an interaction between the bait protein and the prey protein; and observing a difference in fluorescence distribution and intensity in the cell by comparing a control which is not treated with the candidate material, the method being characterized in that: the $1^{st}$ fluorescence protein and the $2^{nd}$ fluorescence protein emit light having different wavelengths from each other; the $1^{st}$ self-assembly protein and the $2^{nd}$ self-assembly protein do not interact with each other; and the $1^{st}$ fluorescence protein or the $2^{nd}$ fluorescence protein is omittable in the case where either the $1^{st}$ fluorescence protein or the $2^{nd}$ fluorescence protein is DsRed.

The difference in distribution and intensity of fluorescence can be observed with naked eyes through a fluorescence microscopy. In the case when nanoclusters are not formed, fluorescence is exhibited in a generally distributed form in the cytoplasm or in cell organelles where expressed proteins are located, while in the case when nanocluster is formed due to interactions between nanoparcitles, the nanocluster is visualized in a dot form showing strong fluorescence. Such changes can be observed with naked eyes, and also a number of fluorescence dots and fluorescence intensity can be quantified through image analysis software.

Advantageous Effects

According to an example of the present disclosure described above, an efficient protein-protein interaction analysis may be performed. Surely, the scope of the present disclosure is not limited by these effects.

BRIEF DESCRIPTION OF THE DRAWINGS

FIG. 3a is a schematic diagram schematically illustrating a nanocluster formation, and FIG. 3b is an image obtained by taking a photograph of a cell with a fluorescence microscopy.

BEST MODE FOR CARRYING OUT THE INVENTION

Figure 1:
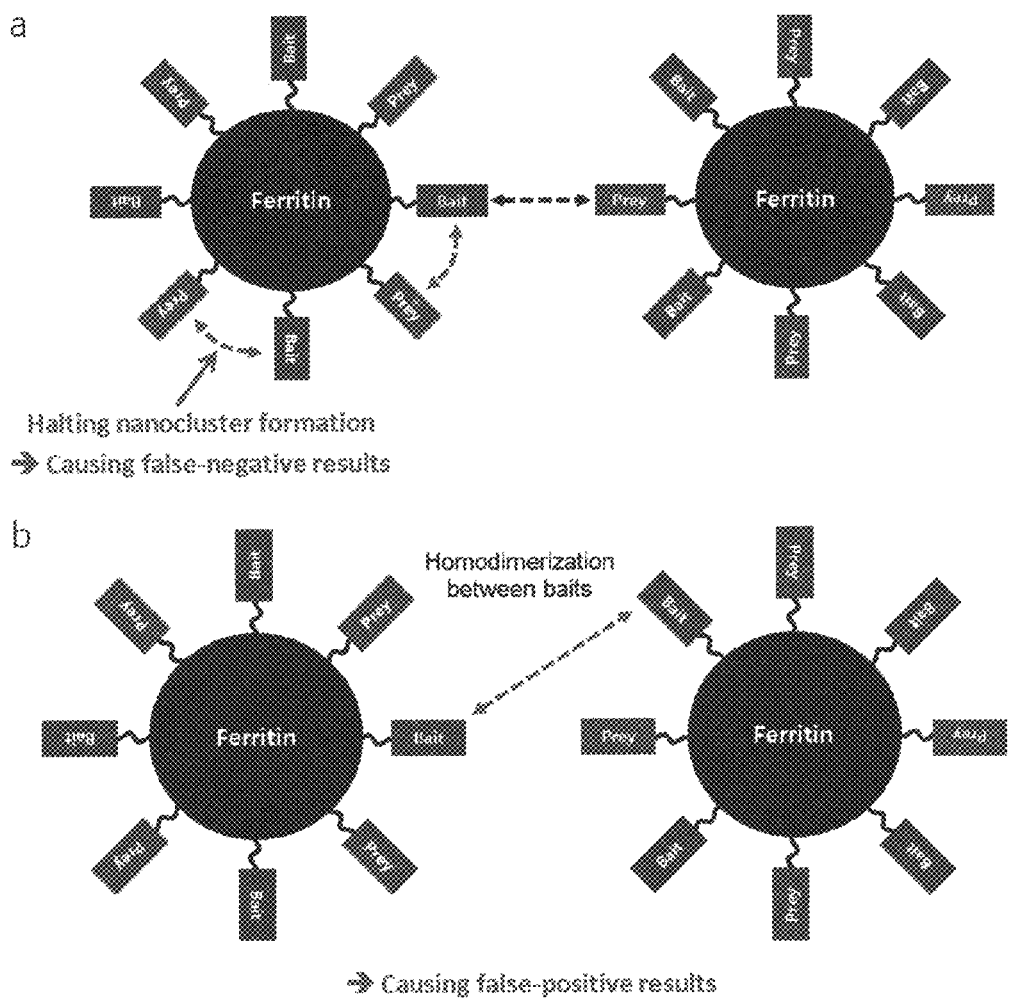
FIGS. 1a and 1b are schematic diagrams showing a drawback of the conventional protein-protein interaction analysis method using a nanocluster.

Description of Terminology
The terms used herein are defined as following.
As used herein, the term "bait protein" means a protein which is used to investigate an interaction with other protein.
As used herein, the term "prey protein" means a protein which is a potential interaction partner of the "bait protein" and becomes target which is investigated (analyzed) or detected.
As used herein, the term "candidate material for regulating an interaction" means a material which is expected to promote, induce, suppress, or inhibit the interaction between "bait protein" and "prey protein".
As used herein, the term "self-assembly protein" means a protein which can be self-assembled concurrent with a protein expression without aid from an intermediate material. A representative example of a self assembly protein includes ferritin.
As used herein, the term "nanocluster" means a group formed by an interaction between nanoparticles, wherein the nanoparticles are formed by self-assembly of the self-assembly protein.

Detailed Description of the Present Invention
According to an aspect of the present disclosure, provided is a kit for analyzing a protein-protein interaction including: a $1^{st}$ expression vector including a $1^{st}$ gene construct having a $1^{st}$ polynucleotide which is operably linked to a promoter and encodes a $1^{st}$ fusion protein having a bait protein, a $1^{st}$ fluorescence protein and a $1^{st}$ self-assembly protein; and a $2^{nd}$ expression vector including a $2^{nd}$ gene construct having a $2^{nd}$ polynucleotide which is operably linked to a promoter, and encodes a $2^{nd}$ fusion protein having a prey protein, a $2^{nd}$ fluorescence protein and a $2^{nd}$ self-assembly protein, the kit being characterized in that: the $1^{st}$ fluorescence protein and the $2^{nd}$ fluorescence protein emit light having different wavelengths from each other; the $1^{st}$ self-assembly protein and the $2^{nd}$ self-assembly protein do not interact with each other; and the $1^{st}$ fluorescence protein or the $2^{nd}$ fluorescence protein is omittable in the case where either the $1^{st}$ fluorescence protein or the $2^{nd}$ fluorescence protein is DsRed.

In the analysis kit, an order of the bait protein, the $1^{st}$ fluorescence protein, and the $1^{st}$ self-assembly protein in the $1^{st}$ fusion protein is irrelevant. For example, the $1^{st}$ fusion protein may be constructed in an order of the bait protein, the $1^{st}$ fluorescence protein, and the $1^{st}$ self-assembly protein or an order of the $1^{st}$ self-assembly protein, the $1^{st}$ fluorescence protein, and the bait protein. Likewise, an order of the prey protein, the $2^{nd}$ fluorescence protein, and the $2^{nd}$ self-assembly protein in the $2^{nd}$ fusion protein is also irrelevant. For example, the $2^{nd}$ fusion protein may be constructed in an order of the prey protein, the $2^{nd}$ fluorescence protein, and the $2^{nd}$ self-assembly protein or an order of the $2^{nd}$ self-assembly protein, the $2^{nd}$ fluorescence protein, and the prey protein.

According to another aspect of the present disclosure, provided is a kit for analyzing a protein-protein interaction including: a $1^{st}$ expression vector including a $1^{st}$ polynucleotide and a multi-cloning site, wherein, the $1^{st}$ polynucleotide is operably linked to a promoter and encodes a $1^{st}$ fusion protein having a $1^{st}$ fluorescence protein and a $1^{st}$ self-assembly protein, and the multi-cloning site is a site where a polynucleotide encoding a bait protein may be operably linked to the polynucleotide encoding the $1^{st}$ fusion protein; and a $2^{nd}$ expression vector including a $2^{nd}$ polynucleotide and a multi-cloning site, wherein, the $2^{nd}$ polynucleotide is operably linked to a promoter and encodes a $2^{nd}$ fusion protein having a $2^{nd}$ fluorescence protein and a $2^{nd}$ self-assembly protein, and the multi-cloning site is a site where a polynucleotide encoding a prey protein may be operably linked to the polynucleotide encoding the $2^{nd}$ fusion protein, the kit being characterized in that the $1^{st}$ fluorescence protein and the $2^{nd}$ fluorescence protein emit light having different wavelengths from each other; the $1^{st}$ self-assembly protein and the $2^{nd}$ self-assembly protein do not interact with each other; and the $1^{st}$ fluorescence protein or the $2^{nd}$ fluorescence protein is omittable in the case where either the $1^{st}$ fluorescence protein or the $2^{nd}$ fluorescence protein is DsRed.

In the analysis kit, the $1^{st}$ fluorescence protein may be a green fluorescent protein (GFP), a yellow fluorescent protein (YFP), a red fluorescent protein (RFP), a cyan fluorescent protein (CFP), a blue fluorescent protein (BFP), ECFP, TagCFP, DsRed or a tetracystein fluorescent motif.

In the analysis kit, the $1^{st}$ self-assembly protein may be ferritin, a virus capsid protein, a ferritin analogue protein, magnetosome, calmodulin kinase IIα (CaMKIIα) or DsRed, and the virus capsid protein may be a CCMV (cowpea chlorotic mottle virus) capsid protein, a norwalk virus capsid protein, a SV40 major capsid protein, or a papilloma virus capsid protein.

In the analysis kit, the $2^{nd}$ fluorescence protein may be a green fluorescent protein (GFP), a yellow fluorescent protein (YFP), a red fluorescent protein (RFP), a cyan fluorescent protein (CFP), a blue fluorescent protein (BFP), ECFP, TagCFP, DsRed or a tetracystein fluorescent motif.

In the analysis kit, the $2^{nd}$ self-assembly protein may be ferritin, a virus capsid protein, a ferritin analogue protein, magnetosome, calmodulin kinase IIα (CaMKIIα) or DsRed, and the virus capsid protein may be a CCMV (cowpea chlorotic mottle virus) capsid protein, a norwalk virus capsid protein, a SV40 major capsid protein, or a papilloma virus capsid protein.

In the analysis kit, the promoter may be a eukaryotic promoter.

According to another aspect of the present disclosure, provided is a method for analyzing a protein-protein interaction, the method including: transfecting a cell with a $1^{st}$ expression vector including a $1^{st}$ gene construct and a $2^{nd}$ expression vector including a $2^{nd}$ gene construct, wherein the $1^{st}$ gene construct including a $1^{st}$ polynucleotide which is operably linked to a promoter and encodes a $1^{st}$ fusion protein having a bait protein, a $1^{st}$ fluorescence protein and a $1^{st}$ self-assembly protein, and the $2^{nd}$ gene construct including a $2^{nd}$ polynucleotide which is operably linked to a promoter and encodes a $2^{nd}$ fusion protein having a prey protein, a $2^{nd}$ fluorescence protein and a $2^{nd}$ self-assembly protein; and observing fluorescence distribution and intensity in the cell with a fluorescence microscopy after culturing the transfected cell, the method being characterized in that: the $1^{st}$ fluorescence protein and the $2^{nd}$ fluorescence protein emit light having different wavelengths from each other; the $1^{st}$ self-assembly protein and the $2^{nd}$ self-assembly protein do not interact with each other; and the $1^{st}$ fluorescence protein or the $2^{nd}$ fluorescence protein is omittable in the case where either the $1^{st}$ fluorescence protein or the $2^{nd}$ fluorescence protein is DsRed.

According to another aspect of the present disclosure, provided is a method for analyzing a protein-protein interaction, the method including: transfecting a cell with a $1^{st}$ expression vector including a $1^{st}$ gene construct and a $2^{nd}$ expression vector including a $2^{nd}$ gene construct, wherein the $1^{st}$ gene construct having a $1^{st}$ polynucleotide which is operably linked to a promoter and encodes a $1^{st}$ fusion protein having a bait protein, a $1^{st}$ fluorescence protein and a $1^{st}$ self-assembly protein, and the $2^{nd}$ gene construct having a $2^{nd}$ polynucleotide which is operably linked to a promoter and encodes a $2^{nd}$ fusion protein having a prey protein, a $2^{nd}$ fluorescence protein and a $2^{nd}$ self-assembly protein; treating the transfected cell with a candidate material for regulating an interaction between the bait protein and the prey protein; and observing a difference in fluorescence distribution and intensity in the cell by comparing a control which is not treated with the candidate material, the method being characterized in that: the $1^{st}$ fluorescence protein and the $2^{nd}$ fluorescence protein emit light having different wavelengths from each other; the $1^{st}$ self-assembly protein and the $2^{nd}$ self-assembly protein do not interact with each other; and the $1^{st}$ fluorescence protein or the $2^{nd}$ fluorescence protein is omittable in the case where either the $1^{st}$ fluorescence protein or the $2^{nd}$ fluorescence protein is DsRed.

In the method for analyzing a protein-protein interaction, the $1^{st}$ fluorescence protein may be a green fluorescent protein (GFP), a yellow fluorescent protein (YFP), a red fluorescent protein (RFP), a cyan fluorescent protein (CFP), a blue fluorescent protein (BFP), ECFP, TagCFP, DsRed or a tetracystein fluorescent motif.

In the method for analyzing a protein-protein interaction, the $1^{st}$ self-assembly protein may be ferritin, a virus capsid protein, a ferritin analogue protein, magnetosome, calmodulin kinase IIα (CaMKIIα) or DsRed, and the virus capsid protein may be a CCMV (cowpea chlorotic mottle virus) capsid protein, a norwalk virus capsid protein, a SV40 major capsid protein, or a papilloma virus capsid protein.

In the method for analyzing a protein-protein interaction, the $2^{nd}$ fluorescence protein may be a green fluorescent protein (GFP), a yellow fluorescent protein (YFP), a red fluorescent protein (RFP), a cyan fluorescent protein (CFP), a blue fluorescent protein (BFP), ECFP, TagCFP, DsRed or a tetracystein fluorescent motif.

In the method for analyzing a protein-protein interaction, the 2$^{nd}$ self-assembly protein may be ferritin, a virus capsid protein, a ferritin analogue protein, magnetosome, calmodulin kinase IIα (CaMKIIα) or DsRed, and the virus capsid protein may be a CCMV (cowpea chlorotic mottle virus) capsid protein, a norwalk virus capsid protein, a SV40 major capsid protein, or a papilloma virus capsid protein.

In the method for analyzing a protein-protein interaction, the promoter may be a eukaryotic promoter.

Figure 2:
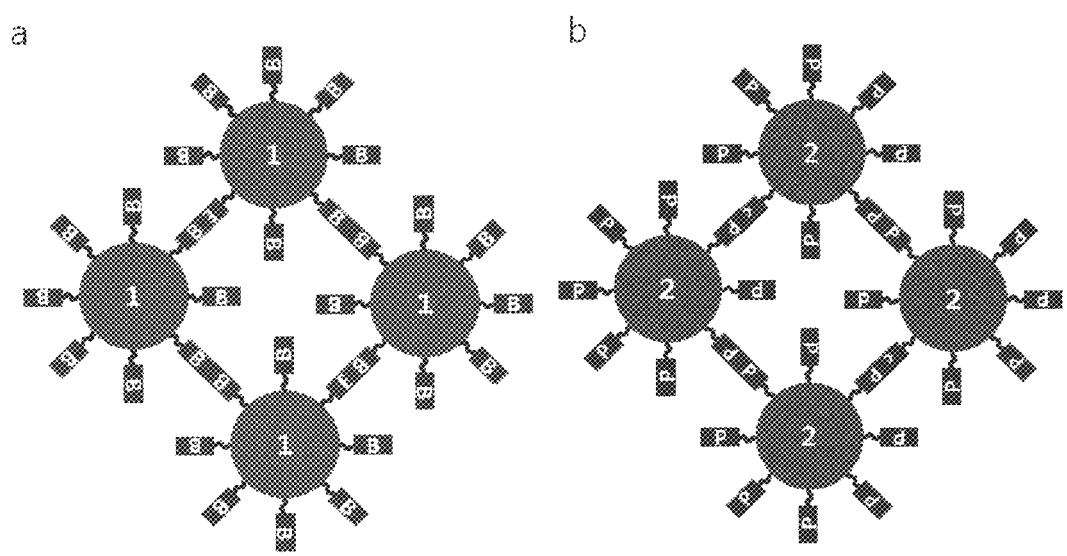
FIGS. 2a and 2b are schematic diagrams showing a benefit of a protein-protein interaction analysis method according to an example of the present disclosure.
Figure 8:
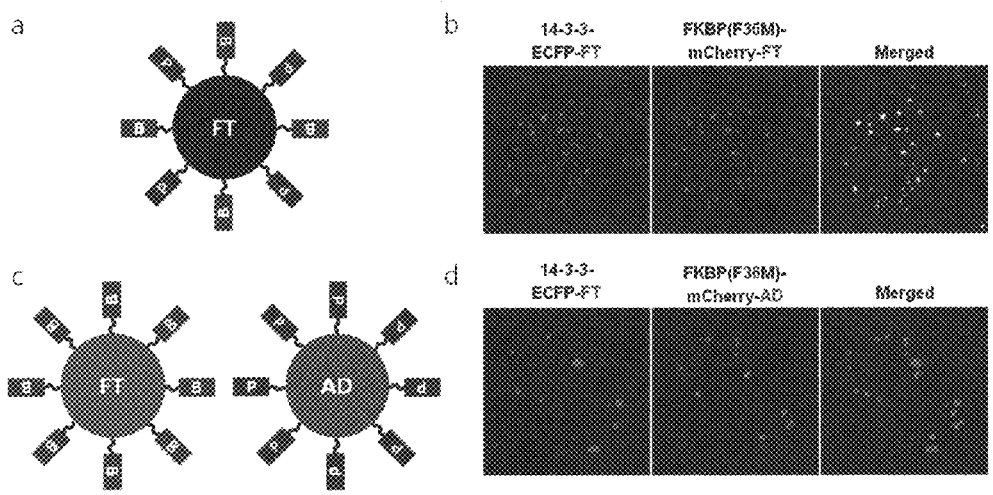
FIG. 8 is a schematic diagram showing a structure of nanoparticles using the analysis method using the conventional nanocluster (FIG. 8a), a schematic diagram showing a structure of nanoparticles according to an example of the present disclosure (FIG. 8b), a fluorescence microscopy image (FIG. 8c) showing a false-positive result due to homodimerization formation for using the analysis method using the conventional nanocluster, and a fluorescence microscopy image showing that whether a result is false-positive or not may be evaluated by using the analysis method according to an example of the present disclosure (FIG. 8d).

The kit and the method of the present disclosure may eliminate risks of false-negative due to interactions between the bait protein and the prey protein preset in one nanoparticle (i.e. failure of a nanocluster formation) (FIG. 1a), and false-positive due to homodimerization between bait proteins and prey proteins in the conventional protein analysis method using nanocluster by using different self-assembly proteins for the bait protein and the prey protein, respectively (FIG. 2a). Also, the present inventors experimentally demonstrate that the risks actually can be eliminated (FIG. 8).

EXAMPLES

Hereinafter, the present disclosure will be described in detail with reference to examples and experimental examples. The present disclosure may, however, be embodied in different forms and should not be construed as limited to the examples and experimental examples set forth herein. Rather, these examples and experimental examples are provided so that this disclosure will be thorough and complete, and will fully convey the scope of the present invention to those skilled in the art.

Example 1

Construction of Vector 1-1: Construction of FKBP-ECFP-FT Construct

FTL (GenBank Acc. No. BC016346), which is a gene for ferritin, was purchased from Open BioSystems Co (USA). A polynucleotide encoding a fusion protein was produced by sequentially fusing an enhanced cyan fluorescent protein (ECFP) and FKBP (FK506 binding protein 1A, GeneBank No. NM_054014.2) into an N-terminal of a ferritin protein. Then, a FKBP-ECFP-FT construct was constructed by inserting the polynucleotide into a pECFP-C1 vector (Clontech, USA) (hereinafter, the ferritin protein is designated by FT).

1-2: Construction of FRB-YFP-CaMKIIα (AD) Construct

Association domain (AD) of CaMKIIα (amino acid residues 315-478) which involves self-assembly of a CaMKIIα gene (GenBank No: NM_012920) was used as a self-assembly protein. A FRB (FKBP12-rapamycin binding) domain was obtained by amplifying an mTOR gene (GenBank No.: NM_004958.3, amino acid residues 2021-2113) and used. A polynucleotide encoding a fusion protein was produced by sequentially fusing FRB, a yellow fluorescent protein (YFP), and CaMKIIα (AD). Then, a FRB-YFP-CaMKIIα construct was constructed by inserting the polynucleotide into a pECFP-C1 vector (Clontech, USA).

1-3: Construction of FRB-ECFP-FT Construct

A polynucleotide was produced by substituting FKBP of the FKBP-ECFP-FT construct constructed in example 1-1 with FRB. Then, a FRB-ECFP-FT construct was constructed by inserting the produced polynucleotide into a pECFP-C1 vector.

1-4: Construction of FKBP-DsRed Construct

A FKBP-DsRed construct was constructed by inserting a gene construct having a polynucleotide encoding DsRed (DsRed-Express2, Strack et al., *Nat. Methods,* 5: 955, 2008) into a pDsRed-Express2-N1 vector (Clonetch, USA), wherein the polynucleotide was operably linked to an end of the FKBP gene.

1-5: Construction of FRB-ECFP-CaMKIIα (AD) Construct

A polynucleotide was produced by substituting the FT gene of the FRB-ECFP-FT construct constructed in example 1-1 with CaMKIIα (AD). Then, a FKBP-ECFP-CaMKIIα construct was constructed by inserting the produced polynucleotide into a pECFP-C1 vector.

1-6: Construction of FRB-DsRed Construct

A polynucleotide was produced by substituting the FKBP gene of the FKBP-DsRed construct constructed in example 1-4 with a FRB gene. Then, a FRB-DsRed construct was constructed by inserting the produced polynucleotide into a pDsRed-Express-N1 vector (Clonetch, USA).

1-7: Construction of DsRed-HRas Construct

A DsRed-HRas construct was constructed by inserting a gene construct having a polynucleotide encoding a HRas gene (GenBank No.: NM_001130442.1, Q61L mutant, CAAX-deleted) into a pDsRed-Express2-C1 vector (Clontech, USA), wherein the polynucleotide was operably linked to an end of the DsRed gene.

1-8: Construction of DsRed-KRas4B Construct

A DsRed-KRas4B construct was constructed by inserting a gene construct having a polynucleotide encoding a KRas4B gene (GenBank No.: NM_033360.2, Q61L mutant, CAAX-deleted) into a pDsRed-Express2-C1 vector (Clontech, USA), wherein the polynucleotide was operably linked to an end of the DsRed gene.

1-9: Construction of DsRed-NRas Construct

A DsRed-NRas construct was constructed by inserting a gene construct having a polynucleotide encoding an NRas gene (GenBank No.: NM_002524.3, Q61L mutant, CAAX-deleted) into a pDsRed-Express2-C1 vector (Clontech, USA), wherein the polynucleotide was operably linked to an end of the DsRed gene.

1-10: Construction of DsRed-MRas Construct

A DsRed-MRas construct was constructed by inserting a gene construct having a polynucleotide encoding an MRas gene (GenBank No.: NM_001085049.1, Q71L mutant, CAAX-deleted) into a pDsRed-Express2-C1 vector (Clontech, USA), wherein the polynucleotide was operably linked to an end of the DsRed gene.

1-11: Construction of DsRed-Rap2B Construct

A DsRed-Rap2B construct was constructed by inserting a gene construct having a polynucleotide encoding a Rap2B gene (GenBank No.: NM_002886.2, G12V mutant, CAAX-deleted) into a pDsRed-Express2-C1 vector (Clontech, USA), wherein the polynucleotide was operably linked to an end of the DsRed gene.

1-12: Construction of DsRed-DiRas3 Construct

A DsRed-DiRas3 construct was constructed by inserting a gene construct having a polynucleotide encoding a DiRas3 gene (GenBank No.: NM_004675.2, A46V mutant, CAAX-deleted) into a pDsRed-Express2-C1 vector (Clontech, USA), wherein the polynucleotide was operably linked to an end of the DsRed gene.

1-13: Construction of DsRed-RheB Construct

A DsRed-RheB construct was constructed by inserting a gene construct having a polynucleotide encoding a RheB gene (GenBank No.: NM_005614.3, Q64L mutant, CAAX-deleted) into a pDsRed-Express2-C1 vector (Clontech, USA), wherein the polynucleotide was operably linked to an end of the DsRed gene.

1-14: Construction of DsRed-Ra1B Construct

A DsRed-Ra1B construct was constructed by inserting a gene construct having a polynucleotide encoding a Ra1B gene (GenBank No.: NM_002881.2, Q72L mutant, CAAX-deleted) into a pDsRed-Express2-C1 vector (Clontech, USA), wherein the polynucleotide was operably linked to an end of the DsRed gene.

1-15: Construction of DsRed-Rap1A Construct

A DsRed-Rap1A construct was constructed by inserting a gene construct having a polynucleotide encoding a Rap1A gene (GenBank No.: NM_001010935.1, G12V mutant, CAAX-deleted) into a pDsRed-Express2-C1 vector (Clontech, USA), wherein the polynucleotide was operably linked to an end of the DsRed gene.

1-16: Construction of $RBD_{Raf1}$-ECFP-FT Construct

A polynucleotide was produced by substituting FKBP of the FKBP-ECFP-FT constructed in example 1-1 with a polynucleotide encoding a Ras association domain ($RBD_{Raf1}$) of a Raf1 protein (GenBank No.: NM_002880.3). Then, an $RBD_{Raf1}$-ECFP-FT construct was constructed by inserting the produced polynucleotide into a pECFP-C1 vector (Clonetch, USA).

1-17: Construction of $CRIB_{WASP}$-ECFP-FT Construct

A polynucleotide was produced by substituting FKBP of FKBP-ECFP-FT constructed in example 1-1 with a polynucleotide encoding a $CRIB_{WASP}$ protein (GenBank No.: NM_000377.2). Then, a $CRIB_{WASP}$-ECFP-FT construct was constructed by inserting the produced polynucleotide into a pECFP-C1 vector (Clonetch, USA).

1-18: Construction of mCherry-CaMKII[296-315]-AD Construct

A polynucleotide encoding a fusion protein was produced, wherein the fusion protein encodes mCherry (Clontech), which express red color in fluorescence microscopy, amino acid residues 296-315 of CaMKIIα, which is known as residues that interact with calmodulin (CaM), and an association domain (AD) which involves self-assembly of CaMKIIα. Then, mCherry-CaMKII[296-315]-AD construct was constructed by inserting the produced polynucleotide into a pmCherry-C1 vector (Clontech, USA).

1-19: Construction of CaM-ECFP-FT Construct

A polynucleotide was produced by substituting the FKBP gene of the FKBP-ECFP-FT construct constructed in example 1-1 with a calmodulin (CaM) gene. Then, a CaM-ECFP-FT construct was constructed by inserting the produced polynucleotide into a pECFP-C1 vector (Clonetch, USA).

Example 2

Transfection 2-1: Transfection of FKBP-ECFP-FT and FRB-YFP-CaMKIIα (AD)

The FKBP-EGFP-FT construct produced in example 1-1 and the FRB-YFP-CaMKIIα (AD) construct produced in example 1-2 were respectively transfected or co-transfected into previously cultured HeLa cells (ATCC No. CCL-2) by using electroporation (1000 V, 35 ms, 2 pulses). Then, cells were plated on a 96-well glass bottom plate (Matrical Bioscience, USA) and incubated for 24 hours in a incubator (37° C., 10% $CO_2$) to express the fusion protein.

2-2: Transfection of FKBP-ECFP-FT and FRB-DsRed

The FKBP-EGFP-FT construct constructed in example 1-1 and the FRB-DsRed construct constructed in example 1-6 were respectively transfected or co-transfected into previously cultured HeLa cells by using electroporation (1000 V, 35 ms, 2 pulses). Then, cells were plated on a 96-well glass bottom plate (Matrical Bioscience, USA) and incubated for 24 hours in a incubator (37° C., 10% CO2) to express the fusion protein.

2-3: Transfection of FKBP-ECFP-CaMKIIα (AD) and FRB-DsRed

The FRB-GFGP-CaMKIIα (AD) construct produced in example 1-4 and the FKBP-DsRed construct produced in example 1-5 were respectively transfected or co-transfected into previously cultured HeLa cells by using electroporation (1000 V, 35 ms, 2 pulses). Then, cells were plated on a 96-well glass bottom plate (Matrical Bioscience, USA) and incubated for 24 hours in a incubator (37° C., 10% $CO_2$) to express the fusion protein.

2-4: Coexpression of Various DsRed-Ras Fusion Proteins and $PRD_{Raf1}$-ECFP-FT Fusion Protein The DsRed-HRas construct constructed in example 1-7 and the $RBD_{Raf1}$-ECFP-FT construct constructed in example 1-16 were respectively transfected or co-transfected into previously cultured HeLa cells by using electroporation (1000 V, 35 ms, 2 pulses). Then, cells were plated on a 96-well glass bottom plate (Matrical Bioscience, USA) and incubated for 24 hours in a incubator (37° C., 10% $CO_2$) to express the fusion protein. As a negative control, the DsRed-HRas construct constructed in example 1-7 and the $CRIB_{WASP}$-ECFP-FT construct constructed in example 1-17 were transfected into HeLa cells by the method same as above.

In addition, the DsRed-KRas4B, DsRed-NRas, DsRed-MRas, DsRed-Rap2B, DsRed-DiRas3, DsRed-RheB or DsRed-Ra1B construct, which are respectively constructed in examples 1-8 to 1-15, and the $RBD_{Raf1}$-ECFP-FT construct constructed in example 1-16 were respectively transfected or co-transfected into previously cultured HeLa cells by using electroporation (1000 V, 35 ms, 2 pulses). Then, cells were plated on a 96-well glass bottom plate (Matrical Bioscience, USA) and incubated for 24 hours in a incubator (37° C., 10% $CO_2$) to express the fusion protein.

Experimental Example 1

Figure 3:
FIG. 3 is a result obtained by observing an interaction between FKBP and FRB by using the protein-protein interaction analysis method according to an example of the present disclosure.
Figure 3:
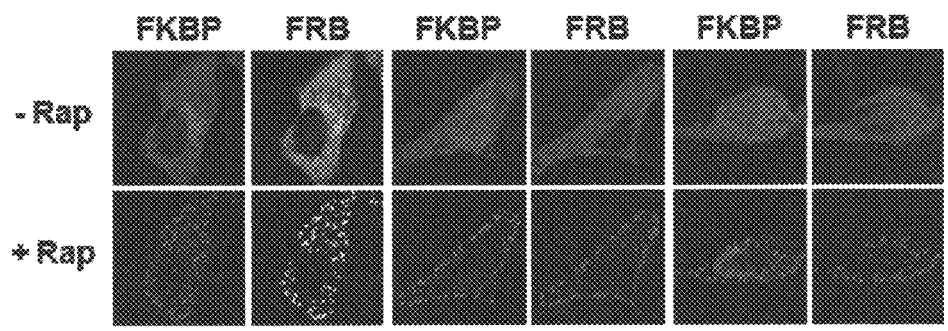

Observation of Presence and Absence of Interaction Between FKBP and FRB by Rapamycin For imaging HeLa cells transfected in examples 2-1 to 2-3, a cell medium was changed from DMEM (Gibco) containing 10% of FBS into OPTI-MEM (Gibco). Thereafter, cells were treated with rapamycin (Calbiochem, USA) having a concentration of 500 nM (dissolved in DMSO, a concentration of stock is 2 mM). Then, distribution and intensity of fluorescence in cells were evaluated by a confocal fluorescence microscopy (Nikon, AIR) (FIG. 3). As a result, as shown in FIG. 3, strong fluorescence in dot forms having irregular sizes was observed at several locations after rapamycine treatment, while fluorescence was exhibited as a distributed form over whole cytoplasm of cells without rapamycin treatment. It means that nanoparticles, which are formed by self-clustering of ferritin, CaMKII or DsRed, form a cluster through an interaction between FKBP and FRB mediated by rapamycin, and therefore the nanoculster was visualized by a fluorescence microscopy.

The experiment shows that the present disclosure may be used to investigate a material for regulating an interaction between proteins which interact by particular signal.

Experimental example 2

Investigation of Ras Molecule Having Interaction with $RBD_{Raf1}$

Figure 4:
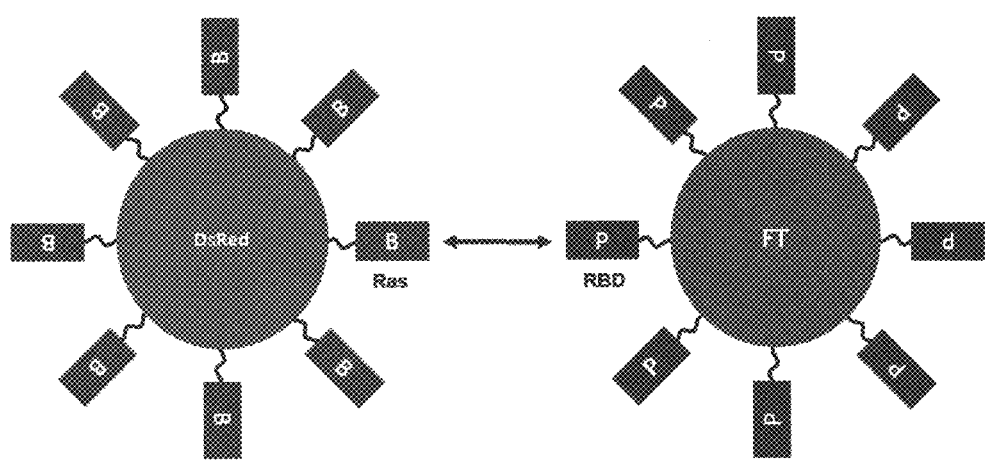
FIG. 4 is a schematic diagram schematically illustrating an operation mode of the analysis method according to an example of the present disclosure which analyzes an interaction between a Ras association domain (RBD) of Raf1 and a Ras protein through the nanocluster formation.

To investigate whether the present disclosure can be used for investigating a prey molecule which interacts with a particular bait molecule without a regulating material of a particular interaction, the present inventors tried to evaluate presence and absence of an interaction between a Ras protein and an $RBD_{Raf1}$ protein of which interaction is known (FIG. 4).

Figure 5:
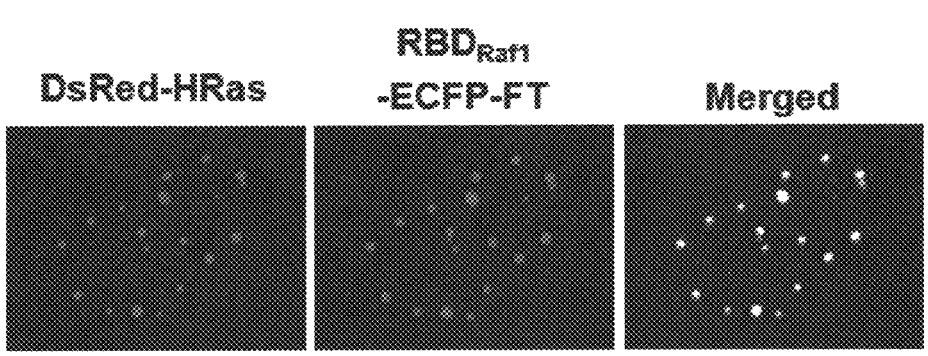
FIG. 5a is an image of a positive control taken by a fluorescence microscopy which shows the interaction between Ras and RBD.
FIG. 5b is an image of a negative control taken by a fluorescence microscopy which shows that Ras and CRIB$_{WASP}$ do not interact.
Figure 5:
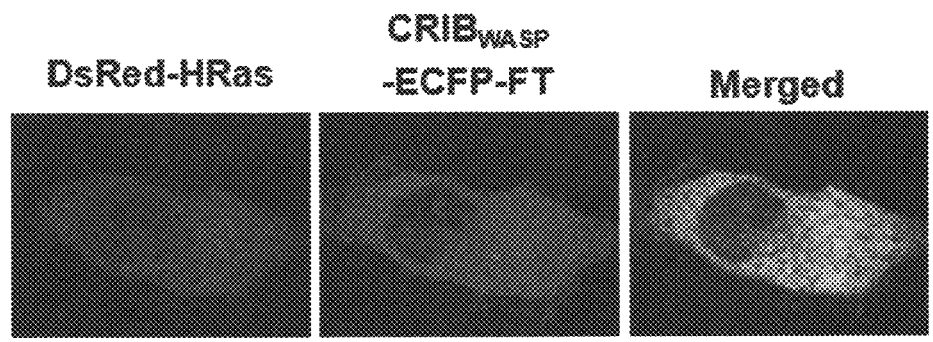

Firstly, distribution and intensity of fluorescence in cells were observed to a cell line cotransfected with a DsRed-HRas construct and a $RBD_{Raf1}$-ECFP-FT construct as a positive control, or a $CRIB_{WASP}$-ECFP-FT construct as a negative control, wherein the DsRed-HRas construct encodes a fusion protein of an HRas protein and DsRed, and the $RBD_{Raf1}$-ECFP-FT construct is known to interact with HRas (FIG. 5). As a result, red fluorescence and cyan fluorescence were exhibited as strong multiple dot forms at the same locations in the case of cells cotransfected with the DsRed-HRas construct and the $RBD_{Raf1}$-ECFP-FT construct (FIG. 5a), while fluorescence was exhibited as a distributed form over whole cytoplasm in the case of cells cotransfected with the Ras-DsRed construct and the $CRIB_{WASP}$-ECFP-FT construct (FIG. 5b). It suggests that a nanoculster was formed between nanoparticles including HRas and RBDRaf1 due to their interactions, and no interaction was occurred between the HRas and $CRIB_{WASP}$ proteins.

Figure 6:
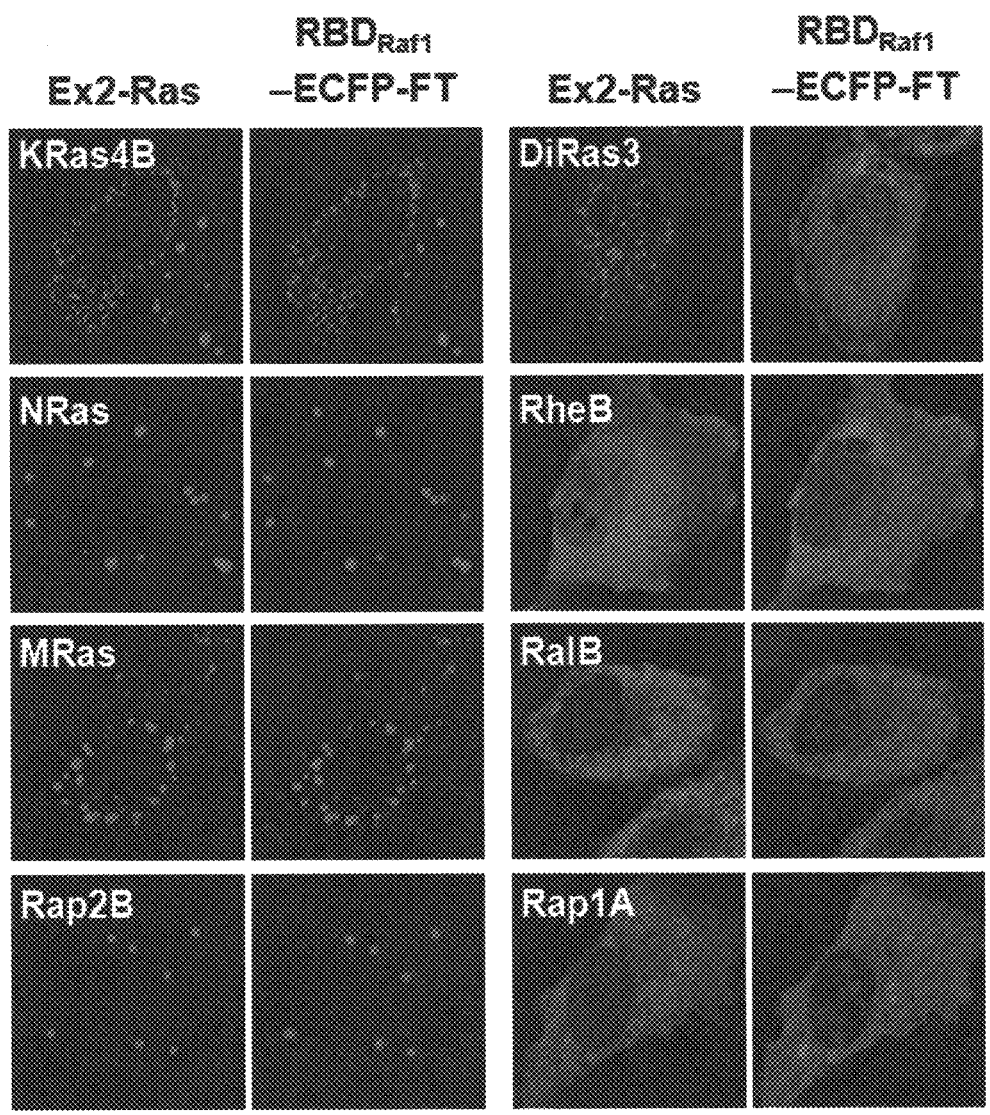
FIG. 6 is a fluorescence microscopy image showing a result of observing presence and absence of interaction between RBD and various Ras analogues through the analysis method according to an example of the present disclosure.

Further, to investigate whether the present disclosure can be used for screening various prey proteins which interact a particular bait protein of the present disclosure, the present inventors observed distribution and intensity of fluorescence in cells cotransfected with the $RBD_{Raf1}$-ECFP-FT construct constructed in example 1-16 and a gene construct expressing a fusion protein of DsRed and various Ras proteins constructed in examples 1-8 to 1-15 (FIG. 6).

As a result, as shown in FIG. 6, red fluorescence and cyan fluorescence were exhibited as multiple dot forms at the same locations in the case of KRas, NRas, MRas and Rap2B, while both red fluorescence and cyan fluorescence were exhibited over whole cytoplasm in the case of RheB, Ra1B and Rap1A. Even some strong dots of red fluorescence were exhibited in cytoplasm in the case of DiRas3, cyan fluorescence of $RBD_{Raf1}$ was exhibited as a distributed form over cytoplasm unlike dot forms of DiRas3, which suggest that there was no interaction.

Form above results, it could be found that $RBD_{Raf1}$ strongly interacts with KRas, NRas, MRas, and Rap2B and does not interact with DiRas3, RheB, Ra1B and Rap1A.

Experimental Example 3

Real-Time Observation of Interaction Between CaMKIIα and CaM

To investigate whether the system of the present disclosure can be used for real-time observation of an intermolecular interaction regulated by calcium through a calcium dependent nanocluster formation, the present inventors cotransfected HeLa cells with the mCherry-CaMKII[296-315]-AD construct constructed in example 1-18 and the CaM-ECFP-FT construct constructed in example 1-19 through the method described above. Thereafter, the cells were treated with 1 mM of ionomycin as ionophore which facilitates calcium ion penetration. Then, distribution and intensity of fluorescence were observed with a fluorescence microscopy (FIGS. 7a and 7b).

Figure 7:
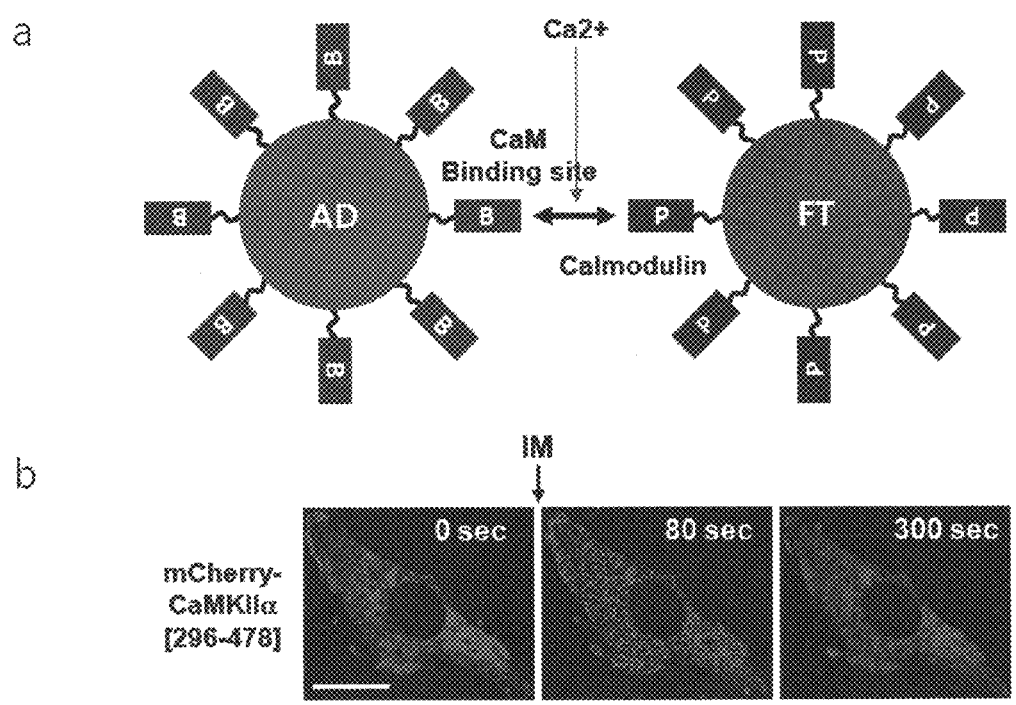
FIG. 7 is a schematic diagram (FIG. 7a) and an actual fluorescence microscopy image (FIG. 7b) showing an example of a protein-protein interaction regulation by a calcium ion by using the analysis method according to an example of the present disclosure.

As a result, as shown in FIG. 7b, fluorescence was distributed in cytoplasm before ionomycin treatment, however, 80 seconds after ionomycin treatment, a strong fluorescence dot appeared in cytoplasm due to a nanocluster formation. Then, fluorescence was distributed again as time passes. From such results, it can be found that an interaction between CaMKIIα and calmodulin was occurred depending on calcium influx, and the interaction was gradually released as calcium was removed.

Comparative Example

Possibility of False-Positive Caused by Homogenous Interaction

The conventional method for analyzing a protein-protein interaction exhibits false-positive due to homodimerization between bait proteins depending on properties of the conventional bait protein and/or prey protein (FIGS. 8a and 8b). To investigate whether the system of the present disclosure can filter such false-positive, a 14-3-3 protein (GenBank No.: NM_139323.2) and a FKBP (F36M) protein, which are known to perform homodimerization, were used.

Specifically, a polynucleotide encoding a fusion protein in which ECFP and FT were sequentially linked was produced. The, a 14-3-3-ECFP-FT construct was constructed by inserting the produced polynucleotide into a pECFP-C1 vector (Clonetch, USA). A polynucleotide encoding a fusion protein in which a FKBP (F36M) protein, mCherry, and FT were sequentially linked and a polynucleotide encoding a fusion protein in which the FKBP (F36M) protein, mCherry, and AD (an association domain of CaMKIIα) were sequentially linked were respectively produced. Then, a FKBP (F36M)-mCherry-FT construct and a FKBP(F36M)-mCherry-AD construct were constructed by respectively inserting the polynucleotide into a pmCherry-C1 vector (Clonetch, USA).

Thereafter, a cell line was produced by cotransfecting HeLa cells with the 14-3-3-ECFP-FT construct and the FKBP(F36M)-mCherry-FT construct and a cell line was produced by cotransfecting HeLa cells with the 14-3-3-ECFP-FT construct and the FKBP(F36M)-mCherry-AD. Then, distribution and intensity of fluorescence of the cell lines were analyzed (FIGS. 8c and 8d). In the conventional system (a combination of the 14-3-3-ECFP-FT construct and the FKBP(F36M)-mCherry-FT construct), cyan fluorescence and red fluorescence in plurality of dot forms were exhibited at the same locations, and thus it appears that an interaction between both proteins occurred (FIG. 8c).

In the system of the present disclosure, however, both cyan fluorescence and red fluorescence were exhibited in particular dot forms at different locations from each other (FIG. 5d). Thus, it could be found that an interaction does not occur between the two proteins.

Such results show that an interaction between heterogeneous proteins and an interaction between homogeneous proteins can be distinguished, since the improved system of the present disclosure uses different self-assembly proteins for each bait protein and prey protein, while a result obtained by an interaction between heterogeneous proteins was not distinguished from a result obtained by an interaction between homogeneous proteins in the conventional system, since only one kind of a self-assembly protein, ferritin, was used, and consequently, the bait protein and the prey protein were co-located in a nanoparticle which was formed by self-assembly of ferritin.

Therefore, it can be found that the system of the present disclosure is a very effective system which significantly decreases a risk of false-positive.

Although the present disclosure has been described with reference to the specific examples and experimental examples, it is not limited thereto. Therefore, it will be readily understood by those skilled in the art that various modifications and changes can be made thereto without departing from the spirit and scope of the present invention defined by the appended claims.

INDUSTRIAL APPLICABILITY

A kit and a method for analyzing a protein-protein interaction according to an example of the present disclosure possibly used as a tool for studying various protein-protein interactions in cells.

The invention claimed is:

1. A kit for analyzing a protein-protein interaction, comprising:
 a $1^{st}$ expression vector including a $1^{st}$ gene construct having a $1^{st}$ polynucleotide which is operably linked to a promoter and encodes a $1^{st}$ fusion protein having a bait protein, a $1^{st}$ fluorescence protein and a $1^{st}$ self-assembly protein; and
 a $2^{nd}$ expression vector including a $2^{nd}$ gene construct having a $2^{nd}$ polynucleotide which is operably linked to a promoter, and encodes a $2^{nd}$ fusion protein having a prey protein, a $2^{nd}$ fluorescence protein and a $2^{nd}$ self-assembly protein,
 wherein the $1^{st}$ fluorescence protein and the $2^{nd}$ fluorescence protein emit light having diffferent wavelengths from each other; the $1^{st}$ self-assembly protein and the $2^{nd}$ self-assembly protein do not interact with each other and the $1^{st}$ self-assembly protein and the $2^{nd}$ self-assembly protein form nanoparticles by self-assembly, respectively; and the $1^{st}$ fluorescence protein or the $2^{nd}$ fluorescence protein is omittable when either the $1^{st}$ fluorescence protein or the $2^{nd}$ fluorescence protein is DsRed, and
 wherein nanoclusters are formed when the nanoparticies interact with each other.

2. The kit of claim 1, wherein the $1^{st}$ fluorescence protein is a green fluorescent protein ((GFP), a yellow fluorescent protein (YFP), a red fluorescent protein (RFP), a cyan fluorescent protein (CFP), a blue fluorescent protein (BFP), ECFP, TagCFP, DsRed or a tetracystein fluorescent motif.

3. The kit of claim 1, wherein the $1^{st}$ self-assembly protein is ferritin, a virus capsid protein, magnetosome, calmodulin kinase IIα (CaMKIIα) or DsRed.

4. The kit of claim 3, wherein the virus capsid protein is a cowpea chlorotic mottle virus (CCMV) capsid protein, a norwalk virus capsid protein, a SV40 major capsid protein, or a papilloma virus capsid protein.

5. The kit of claim 1, wherein the $2^{nd}$ fluorescence protein is a green fluorescent protein (GFP), a yellow fluorescent protein (YFP), a red fluorescent protein (RFP), a cyan fluorescent protein (CFP), a blue fluorescent protein (BFP), ECFP, TagCFP, DsRed or a tetracystein fluorescent motif.

6. The kit of claim 1, wherein the $2^{nd}$ self-assembly protein is ferritin, a virus capsid protein, maenetosome, calmodulin kinase IIα (CaMKIIα) or DsRed.

7. The kit of claim 6, wherein the virus capsid protein is a CCMV (cowpea chlorotic mottle virus) capsid protein, a norwalk virus capsid protein, a SV40 major capsid protein, or a papilloma virus capsid protein.

8. The kit of claim 1, wherein the promoter is a eukaryotic promoter.

9. The kit of claim 1, wherein the promoter is a eukaryotic promoter.

10. A kit for analyzing a protein-protein interaction, comprising:
 a $1^{st}$ expression vector including a $1^{st}$ polynucleotide and a multi-cloning site, wherein, the $1^{st}$ polynucleotide is operably linked to a promoter and encodes a $1^{st}$ fusion protein having a $1^{st}$ fluorescence protein and a $1^{st}$ self assembly protein, and the multi-cloning site is a site where a polynucleotide encoding a bait protein may be operably linked to the polynucleotide encoding the $1^{st}$ fusion protein; and
 a $2^{nd}$ expression vector including a $2^{1}$ polynucleotide and a multi-cloning site, wherein, the $2^{nd}$ polynucleotide is operably linked to a promoter and encodes a $2^{nd}$ fusion protein having a $2^{1}$ fluorescence protein and a $2^{nd}$ self-assembly protein, and the multi-cloning site is a site where a polynucleotide encoding a prey protein may be operably linked to the polynucleotide encoding the $2^{nd}$ fusion protein,
 wherein the $1^{st}$ fluorescence protein and the $2^{nd}$ fluorescence protein emit light having diffferent wavelengths from each other; the $1^{st}$ self-assembly protein and the $2^{nd}$ self-assembly protein do not interact with each other and the $1^{st}$ self-assembly protein and the $2^{nd}$ self-assembly protein form nanoparticles by self-assembly, respectively; and the $1^{st}$ fluorescence protein or the $2^{nd}$ fluorescence protein is omittable when either the $1^{st}$ fluorescence protein or the $2^{nd}$ fluorescence protein is DsRed, and wherein nanociusters are formed when the nanoparticles interact with each other.

11. The kit of claim 2, wherein the $1^{st}$ fluorescence protein is a green fluorescent protein (GFP), a yellow fluorescent protein (YFP), a red fluorescent protein (RFP), a cyan fluorescent protein (CFP), a blue fluorescent protein (BFP), ECFP, TacCFP, DsRed or a tetracystein fluorescent motif.

12. The kit of claim 10, wherein the $1^{st}$ self-assembly protein is ferritin, a virus capsid protein, magnetosome, calmodulin kinase IIα (CaMKIIα) or DsRed.

13. The kit of claim 12, wherein the virus capsid protein is a cowpea chlorotic mottle virus (CCMV) capsid protein, a nor alk virus capsid protein, a SV40 major capsid protein, or a papilloma virus capsid protein.

14. The kit of claim 10, wherein the $2^{nd}$ fluorescence protein is a green fluorescent protein (GFP), a yellow fluorescent protein (YFP), a red fluorescent protein (RFP), a cyan fluorescent protein (CFP), a blue fluorescent protein (BFP), ECFP, TagCFP DsRed or a tetracystein fluorescent motif.

15. The kit of claim 10, wherein the $2^{nd}$ self-assembly protein is ferritin, a virus capsid protein, magnetosome, calmodulin kinase IIα (CaMKIIα) or DsRed.

16. The kit of claim 15, wherein the virus capsid protein is a CCMV chlorotic mottle virus) capsid protein, a norwalk virus capsid protein, a SV40 major capsid protein, or a papilloma virus capsid protein.

17. A method for analyzing a protein-protein interaction, comprising:
 transfecting a cell with a $1^{st}$ expression vector including a $1^{st}$ gene construct and a $2^{nd}$ expression vector including a $2^{nd}$ gene construct, wherein the $1^{st}$ gene construct having a 1$^{st}$ polynucleotide which is operably linked to a promoter and encodes a 1$^{st}$ fusion protein having a bait protein, a 1$^{st}$ fluorescence protein and a 1$^{st}$ self-assembly protein, and the 2$^{nd}$ gene construct having a 2$^{nd}$ polynucleotide which is operably linked to a promoter and encodes a 2$^{nd}$ fusion protein having a prey protein, a 2$^{nd}$ fluorescence protein and a 2$^{nd}$ self-assembly protein;

culturing the transfected cell; and observing distribution and intensity of fluorescence in the cell with a fluorescence microscopy, wherein the 1$^{st}$ fluorescence protein and the 2$^{nd}$ fluorescence protein emit light having different wavelengths from each other; the 1$^{st}$ self-assembly protein and the 2$^{nd}$ self-assembly protein do not interact with each other and form nanoparticles by self-assembly, respectively; and the 1$^{st}$ fluorescence protein or the 2$^{nd}$ fluorescence protein is omittable when either the 1$^{st}$ fluorescence protein or the 2$^{nd}$ fluorescence protein is DsRed, and wherein nanoclusters are formed when the nanoparticles interact with each other.

18. The method of claim 17, wherein the 1$^{st}$ fluorescence protein is a green fluorescent protein (GFP), a yellow fluorescent protein (YFP), a red fluorescent protein (RFP), a cyan fluorescent protein (CFP), a blue fluorescent protein (BFP), ECFP, TagCFP, DsRed or a tetracystein fluorescent motif.

19. The method of claim 17, wherein the 1$^{st}$ self-assembly protein is ferritin, a virus capsid protein, magnetosome, calmodulin kinase IIα (CaMKIIα) or DsRed.

20. The method of claim 19, wherein the virus capsid protein is a cowpea chlorotic mottle virus (CCMV) capsid protein, a nor alk virus capsid protein, a SV40 major capsid protein, or a papilloma virus capsid protein.

21. The method of claim 17, wherein the 2$^{nd}$ fluorescence protein is a green fluorescent protein (GFP), a yellow fluorescent protein (YFP), a red fluorescent protein (RFP), a cyan fluorescent protein (CEP), a blue fluorescent protein (BFP), ECFP, TagCFP, DsRed or a tetracystein fluorescent motif.

22. The method of claim 17, wherein the 2$^{nd}$ self-assembly protein is ferritin, a virus capsid protein, magnetosome, calmodulin kinase IIα (CaMKIIα) or DsRed.

23. The method of claim 22, the virus capsid protein is a cowpea chlorotic mottle virus (CCMV) capsid protein, a norwalk virus capsid protein, a SV40 major capsid protein, or a papilloma virus capsid protein.

24. The method of claim 17, wherein the promoter is a eukaryotic promoter.

\* \* \* \* \*